United States Patent [19]  [11] 3,983,104
Vorbruggen  [45] Sept. 28, 1976

[54] N[6]-SUBSTITUTED ADENOSINES
[75] Inventor: Helmut Vorbruggen, Berlin, Germany
[73] Assignee: Schering Aktiengesellschaft, Berlin & Bergkamen, Germany
[22] Filed: Oct. 6, 1972
[21] Appl. No.: 295,719

[30] Foreign Application Priority Data
Oct. 8, 1971  Germany.............................. 2151013

[52] U.S. Cl................................... 536/24; 424/180
[51] Int. Cl.$^2$.......................................... C07H 19/16
[58] Field of Search .............................. 260/211.5 R

[56] References Cited
UNITED STATES PATENTS
3,472,838  10/1969  Hanessian ...................... 260/211.5 R
3,590,029  6/1971  Koch et al. ..................... 260/211.5 R
3,706,728  12/1972  Fauland et al. ................. 260/211.5 R Primary Examiner—Johnnie R. Brown
Attorney, Agent, or Firm—Millen, Raptes & White

[57] ABSTRACT
Novel N[6]-substituted adenosines and a novel process for the preparation of N[6]-substituted adenosines from 6-trialkylsiloxypurine derivatives. The derivatives are reacted in the presence of a tertiary base or a Lewis acid with ammonia or an amine of the formula $HNR_1R_2$, wherein $R_1$ and $R_2$ are the same or different represent hydrogen, alkyl of 1–6 carbon atoms, aralkyl or 7 to 10 carbon atoms unsubstituted or substituted with hydroxy or alkoxy with 1–4 carbon atoms, aryl unsubstituted or substituted with hydroxy or alkoxy with 1 to 4 carbon atoms, a heterocyclic ring of 4 to 7 members, containing a total of 1–3 hetero atoms which can be nitrogen, oxygen or sulfur; or when $R_1$ is hydrogen $R_2$ is hydroxyl, amino, alkyl of 1–4 carbon atoms substituted in the terminal position with a mono- or dialkylamino group, containing 1–4 carbon atoms in each alkyl group, or mono- or bicyclic heterocyclic group of 5–10 members, containing a total of 1–3 hetero atoms, which can be nitrogen, oxygen and sulfur, or $R_1$ and $R_2$, together with the N-atom, collectively represent a heteromonocyclic ring of 4–7 members containing a total of 1–3 hetero atoms which, in addition to the nitrogen atom, can be nitrogen, oxygen or sulfur, unsubstituted or substituted by an alkyl group with 1–4 carbon atoms. The compounds of the invention have valuable biological properties such as cytokinins, etc.

10 Claims, No Drawings

N⁶-SUBSTITUTED ADENOSINES

BACKGROUND OF THE INVENTION

The N⁶-substituted adenosines are of great significance due to their advantageous biological properties, e.g. as cytokinins, and as CNS-active and/or cardiac-circulation-active substances.

These compounds are generally produced by reaction with amines from the 6-halo- or 6-alkyl-mercaptopurine nucleosides, prepared in several stages from inosine and/or guanosine (W.W. Zorback and R. S. Tipson, Interscience Publ. New York [1968], pp. 210, 242, 258). Considering the large number of stages in these syntheses, the processes are expensive and complicated.

SUMMARY OF THE INVENTION

This invention relates to a novel, improved process for the preparation of N⁶-substituted adenosines as well as to novel N⁶-substituted adenosines.

It has now been found by the process of this invention, that inosines silylated in the 6-position and/or guanosines disilylated in the 2- and 6-positions can be reacted under direct heating with ammonia or primary anad secondary amines to produce the N⁶-substituted adenosine. Preferably, the reaction is conducted in the presence of Lewis acids and tertiary amines, such as metallic oxides or metallic salts, e.g. acidic aluminum oxide, mercury(II) chloride, zinc(II) chloride, tin(IV) chloride, and boron trifluoride etherate. The reaction can also take place in the presence of salts of primary, secondary, and tertiary aliphatic as well as aromatic amines with strong inorganic or organic acids, such as, for example, ammonium sulfate, tryptamine hydrochloride, and pyridinium chloride. In this process, it is unimportant in the reaction whether the sugar residue in the inosines or guanosines is present in a free or blocked form, since the free hydroxy groups in the sugar residue are similarly silylated, and the silyl groups can be readily split off again after the reaction. Therefore it is possible, starting with the unblocked inosines or guanosines, to obtain the free N⁶-substituted adenosines directly.

DETAILED DESCRIPTION

Accordingly, this invention relates to a process for the preparation of N⁶-substituted adenosines of the general Formula I

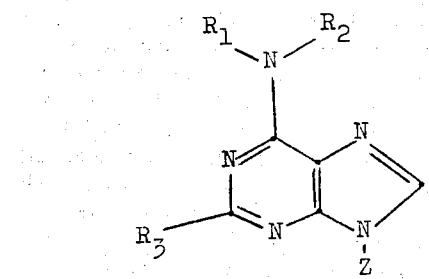

wherein $R_1$ and $R_2$ being the same or different represent hydrogen, alkyl of 1 – 6 carbon atoms, aralkyl of 7 to 10 carbon atoms unsubstituted or substituted with hydroxy or alkoxy with 1 – 4 carbon atoms, aryl unsubstituted or substituted with hydroxy or alkoxy with 1 to 4 carbon atoms, a heterocyclic ring of 4 to 7 members, containing a total of 1 – 3 hetero atoms which can be nitrogen, oxygen or sulfur; or when $R_1$ is hydrogen $R_2$ is hydroxyl, amino, alkyl or 1 – 4 carbon atoms substituted in the terminal position with a mono- or dialkylamino group, containing 1 – 4 carbon atoms in each alkyl group, or a mono- or bicyclic heterocyclic group of 5 – 10 members, containing a total of 1 – 3 hetero atoms, which can be nitrogen, oxygen and sulfur, or $R_1$ and $R_2$, together with the N-atom, collectively represent a heteromonocyclic ring of 4 – 7 members containing a total of 1 – 3 hetero atoms which, in addition to the nitrogen atom, can be nitrogen, oxygen or sulfur, unsubstituted or substituted by ana alkyl group with 1 – 4 carbon atoms, $R_3$ represents hydrogen or amino, and Z represents a free or blocked sugar residue.

Typical $R_1$ and $R_2$ substituents include methyl, ethyl, propyl, butyl, phenyl, p-methoxyphenyl, benzyl, p-methoxybenzyl, p-hydroxybenzyl, homoveratryl, 3-indolylethyl, N,N-dimethylaminoethyl, etc.

Typical heteromonocyclic substituents comprised of $R_1$ and $R_2$ together include pyrrolidine, piperidine, morpholine, hexemethyleneimine, piperazine, etc.

The N⁶-substituted adenosines are prepared by reacting a 6-trialkylsilyloxypurine derivative of the general Formula II

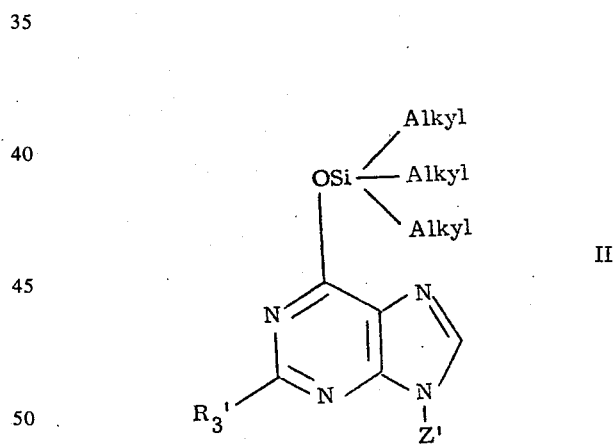

wherein the alkyl residues are the same and each alkyl is of 1 to 3 carbon atoms, preferably methyl, $R_3'$ represents hydrogen or trialkylsilylamino group wherein the alkyl is of 1 to 3 carbon atoms, $Z'$ represents a silylated or acylated sugar residue, or a sugar residue blocked by acetal formation.

The derivative is reacted with ammonia or an amine of the formula $HNR_1R_2$ wherein $R_1$ and $R_2$ have the above designations, or optionally with a salt of the amine, in the presence of a tertiary base, preferably with the use of an amine salt or a Lewis acid as the catalyst; and subsequently optionally removing the blocking groups on the sugar.

Particularly suitable as blocking groups are the trimethylsilyl groups because they can easily be removed. The starting compounds of general Formula II, silylated on the sugar residue, are obtained by reacting free inosine or guanosine, for example, with hexamethyldisilazane (HMDS) in the presence of trimethylchlorosilane or ammonium salts and optionally in the presence of a tertiary base, such as pyridine. The 6-trimethylsilyloxy group and the blocking groups are then introduced simultaneously.

It is unnecessary in the reaction of this invention to isolate the starting compounds of general Formula II. The 6-trialkylsilyloxyguanosines or iosines formed in situ can be reacted in the reaction solution with ammonia or with an amine directly to produce the corresponding adenosines.

The reaction conditions depend on the compund $HNR_1R_2$ and the catalyst. The reaction of the silyl compound of the general Formula II with primary or secondary amines is conducted at 0°–180°C, preferably 20 to 150°C. When using salts of primary and secondary amines, the process is effected in the presence of a tertiary amine, wherein the amine salt can simultaneously serve as the catalyst. Examples of suitable tertiary amines include trimethylamine, triethylamine, ethyldiisopropylamine pyridine, quinoline, etc. Examples and preferred suitable primary amines include methylamine, ethylamine, propylamine, butylamine, aniline, p-anisidine, benzylamine, homoveratrylamine, tryptamine, N,N-dimethylethylenediamine, etc. Examples of and preferred secondary amines include dimethylamine, diethylamine, pyrrolidine, piperidine, morpholine, hexamethylenimine, N-methylpiperazine, etc.

Since the primary amines react with the silylating agent, the primary amine must be added after the formation of the silyl compound of general Formula II and removal of the silylating reagent. In contrast to the primary amines, the secondary amines react only slowly with the silylation agent. Therefore, the silylating agent and the secondary amine can optionally be employed simultaneously.

The reaction with the ammonia is effected under an increased $NH_3$ pressure of about 20–50, preferably 25 to 35, atmospheres gauge. The reaction is terminated after 20–80 hours at 0°–180°C. When the silylation is conducted with hexamethyldisilazane, wherein ammonia is liberated, the silylation and the reaction with ammonia can be carried out in a single stage.

Especially suitable as a solvent for the reaction is excess amine $HNR_1R_2$; however, it is also possible to use solvents, such as, toluene, xylene, anisole, dioxane, glyme, pyridine, or, for the less soluble silyl compounds, preferably dimethylformamide or sulfolane.

Suitable catalysts are the Lewis acids, especially metallic oxides, metallic salts, and salts of amines. The metallic salts are optionally employed in the reaction together with excess amine $HNR_1R_2$. The catalysts are used in the reaction in amounts of 0.001 mol to 5 mols, based on the nucleoside, but preferably in amounts of 0.05 to 1 mol. The most effective and preferred catalysts are acidic aluminum oxide, mercury(II) chloride, mercury(II) acetate, as well as zinc(II) chloride, tin-(IV) chloride, titanium(IV) chloride, and boron trifluoride etherate, utilized in combination with an excess of the amine, and salts of amines, such as, e.g. ammoniam sulfate, tryptamine hydrochloride, pyridinium chloride, etc.

Furthermore this invention embraces novel compounds of the general formula I a

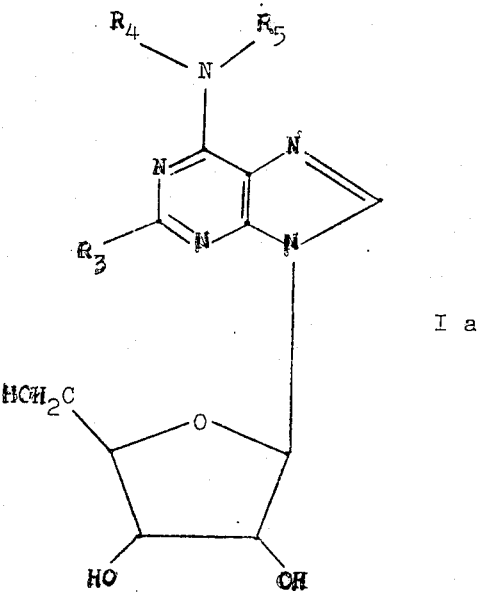

I a wherein
$R_3$ represents hydrogen or amino, and
$R_4$ and $R_5$, together with the n-atom, collectively represent a heteromonocyclic ring of 5 – 7 members or a heteromonocyclic ring of 5 – 7 members containing a further oxygen-or nitrogen atom, the nitrogen atom being unsubstituted or substituted by a methyl group.

Preferred compounds of the formula I a are $N^6$-butylidene-2-amino-adenosine, $N_6$-butylidene-adenosine, 6-(4-N-methyl-piperazine)-9-β-D-ribofuranosyl-purine, 6-(4-N-methyl-piperazino)-2-amino-9-β-D-ribofuranosyl-purine, 6-piperidino-9-β-D- ribofuranosyl-purine, 6-piperidino-2-amino-9-β-D- ribofuranosyl-purine, 6-morpholino-9-β-D-ribofuranosyl-purine and 6-morpholino-2-amino-9-β-D- ribofuranosylpurine.

EXAMPLE 1

$N^6$-(β-3,4-Dimethoxyphenethyl)-2-aminoadenosine 5.6 g. of guanosine was dissolved in 100 ml. of hexamethyldisilazane and 10 ml. of pyridine by heating the reaction mixture for 20 hours to a bath temperature of 160° C.; the solvents were evaporated, and the residue was heated, after the addition of 20 ml. of homoveratrylamine, for 122 hours to 160° C. under a nitrogen atmosphere. After two hours of refluxing with 300 ml. of methanol, the reaction mixture was evaporated and the dark residue extracted three times with respectively 200 ml. of water at 100° C. under agitation. After removal of the water by evaporation, the residue was chromatographed on silica gel with ethyl acetate/ethanol, thus obtaining 1.96 g. (22% of theory) of $N^6$-(β-3,4-dimethoxyphenethyl)-2-aminoadenosine, m.p. 88°–90° C.

EXAMPLE 2

N⁶-(β-phenethyl)adenosine 5.36 g. of inosine was dissolved in 100 ml. of hexamethyldisilazane and 0.5 ml. of trimethylchlorosilane by boiling the reaction mixture for 56 hours at a bath temperature of 155° C. The solvent was distilled off, and the residue was agitated under a nitrogen atmosphere at a bath temperature of 145° C. with 7.36 ml. of β-penethylamine and 0.638 g. of mercury(II) acetate for 22 hours. The brown, clear solution was concentrated by evaporation, the residue was refluxed for three hours in 250 ml. of methanol, and decolorized with active carbon. Upon cooling, 6.67 g. (89.8% of theory) of N⁶-(β-phenethyl)adenosine was crystallized, m.p. 165°–167° C.

EXAMPLE 3

2-Aminoadenosine 5.6 g. of guanosine was dissolved in 100 ml. of hexamethyldisilazane and 0.5 ml. of trimethylchlorosilane by heating the reaction mixture for 6 hours to a bath temperature of 160° C. The solvents were evaporated, and the thus-crystallized residue was heated, after the addition of 0.546 g. of anhydrous zinc(II) chloride and saturation with dry ammonia, in an autoclave to 160° C./25 atmospheres gauge for 18 hours. After cooling, the substance was refluxed in methanol for 5 hours, treated with a small amount of carbon, and filtered. After removing the methanol by evaporation, the residue was recrystallized from aqueous ammonia, thus producing 4.17 g. (74% of theory) of 2-aminoadenosine, m.p. 238°–240° C.

EXAMPLE 4

N⁶-(β-Phenethyl)-2-aminoadenosine 5.67 g. of guanosine was refluxed in 100 ml. of hexamethyldisilazane and 0.5 ml. of trimethylchlorosilane for 16 hours at a bath temperature of 160° C. The reagents were removed under normal pressure, and the residue was agitated with 7.36 ml. of β-phenethylamine and 0.638 g. of mercury(II) acetate under a nitrogen atmosphere at 145° C. for 22 hours. The deep-brown solution was refluxed in 250 ml. of methanol for 4 hours, decolorized with active carbon, and the residue obtained after removing the methanol by evaporation was chromatographed on silica gel in chloroform/methanol, thus obtaining 5.49 g. (71% of theory) of N⁶-(β-phenethyl)-2-aminoadenosine.

EXAMPLE 5

N⁶-(β-3,4-Dimethoxyphenethyl)adenosine 5.36 g. of inosine was dissolved in 100 ml. of hexamethyldisilazane and 0.5 ml. of trimethylchlorosilane by heating the reaction mixture for 18 hours to 155° C. The reagents were distilled off, and the residue was agitated with 10 ml. of homoveratrylamine and 0.543 g. of mercury(II) chloride for 20 hours at a bath temperature of 145° C. and under a nitrogen atmosphere. The brown solution was refluxed in 300 ml. of methanol for 4 hours, treated with carbon, and the residue was recrystallized from water after removing the filtrate by evaporation, thus producing 5.63 g. (67.5% of theory) of N⁶-(β-3,4-dimethoxyphenethyl)adenosine, m.p. 122° C.

EXAMPLE 6

N⁶-(β-3,4-Dimethoxyphenethyl)-2-aminoadenosine 5.67 g. of guanosine was dissolved in 100 ml. of hexamethyldisilazane and 0.5 ml. of trimethylchlorosilane by heating the reaction mixture for 18 hours to 155° C. The reagents were distilled off, and the residue was agitated under a nitrogen atmosphere with 10 ml. of homoveratrylamine and 0.53 g. of mercury(II) chloride for 21 hours at 145° C. The deep-brown solution was refluxed for 5 hours in 250 ml. of methanol, and the residue was chromatographed on silica gel in chloroform/methanol after first removing the methanol by evaporation, thus obtaining 6.06 g. (68% of theory) of N⁶-(β-3,4-dimethoxyphenethyl)-2-aminoadenosine.

EXAMPLE 7

N⁶-(β-Phenethyl)adenosine 2.68 g. of inosine was dissolved in 50 ml. of hexamethyldisilazane and 0.5 ml. of trimethylchlorosilane by heating the reaction mixture for 18 hours to 155° C. The reagents were distilled off, and the residue was mixed with 3.68 ml. of β-phenethylamine and, at 5° C., gently with 0.13 ml. of tin (IV) chloride. After heating for 22 hours under nitrogen to 145° C. bath temperature, the dark residue was refluxed for 3 hours in 100 ml. of methanol, decolorized with carbon, and, after concentration of the filtrate, recrystallized from methanol. In this way, 2.59 g. (69.8% of theory) of N⁶-(β-phenethyl)adenosine was obtained, m.p. 167° C.

EXAMPLE 8

N⁶-(β-Phenethyl)adenosine 5.36 g. of inosine was dissolved in 100 ml. of hexamethyldisilazane and 0.5 ml. of trimethylchlorosilane by heating the reaction mixture for 18 hours to 155° C. The reagents were distilled off, and the residue was heated with 7.36 ml. of β-phenethylamine and 0.264 g. of ammonium sulfate for 21 hours to a bath temperature of 145° C. The reaction mixture was decolorized by means of carbon after refluxing for 3 hours in 300 ml. of methanol, and, after concentration of the filtrate, recrystallized from methanol, thus producing 3.72 g. (50.3% of theory) of N⁶-(β-phenethyl)adenosine, m.p. 167° C.

EXAMPLE 9

N⁶-(β-Phenethyl)adenosine 2.68 g. of inosine was dissolved in 50 ml. of hexamethyldisilazane and 0.5 ml. of trimethylchlorosilane by heating the reaction mixture for 18 hours to 155° C. The reagents were distilled off, and the residue was agitated with 3.68 ml. of β-phenethylamine and 0.113 ml. of boron trifluoride etherate for 20 hours at 145° C. under a nitrogen atmosphere. The reaction mixture was refluxed for 4 hours in 200 ml. of methanol, decolorized with carbon, and, after concentrating the filtrate, recrystallized from methanol, thus obtaining 2.18 g. (56% of theory) of N⁶-(β-phenethyl)adenosine, m.p. 167° C.

EXAMPLE 10

N⁶,N⁶-tetramethylene-2-aminoadenosine 5.67 g. of guanosine in 100 ml. of hexamethyldisilizane and 0.5 ml. of trimethylchlorosilane was refluxed for 16 hours at 155° C. The reagents were distilled off, and the residue was heated with 10 ml. of pyrrolidine and 273 mg. of zinc chloride for 22 hours to 145° C. under a nitrogen atmosphere and under agitation. After distilling off the excess pyrrolidine, the residue was refluxed for 4 hours in 300 ml. of methanol and evaporated. The thus-formed residue was chromatographed on silica gel with chloroform/methanol (5%), thus obtaining 2.48 g. (37% of theory) of $N^6$, $N^6$-tetramethylene-2-aminoadenosine.

EXAMPLE 11

$N^6$-Phenyl-2-aminoadenosine 5.67 g. of guanosine was dissolved in 100 ml. of hexamethyldisilazane and 0.5 ml. of trimethylchlorosilane by 18 hours of refluxing. The reagents were distilled off, and the residue was stirred with 5.5. ml. of aniline and 0.273 g. of zinc chloride for 22 hours at a bath temperature of 145° C. under nitrogen. The reaction mixture was refluxed for 4 hour in 300 ml. of methanol with 2 ml. of triethylamine. Thereafter, dark crystals of unreacted guanosine precipitated overnight, which were filtered off. The filtrate was concentrated by evaporation, extracted with chloroform, and chromatographed on silica gel with chloroform/methanol, thus obtaining 1.4 g. (19.5% of theory) of $N^6$-phenyl-2-aminoadenosine.

EXAMPLE 12

$N^6$-($\beta$-Phenethyl)adenosine 2.68 g. of inosine was dissolved in 100 ml. of hexamethyldisilazane and 0.5 ml. of trimethylchlorosilane by 16 hours of refluxing. The reagents were distilled off, and the residue was heated with 3.68 ml. of $\beta$-phenethylamine and 200 mg. of acidic aluminum oxide (Woelm, AI) for 22 hours under agitation and nitrogen to 145° C. After 3 hours of boiling in 100 ml. of methanol, the solution was treated with carbon and filtrate crystallized, thus producing 1.272 g. (34.3% of theory) of $N^6$-($\beta$-phenethyl)adenosine, m.p. 167° C.

EXAMPLE 13

$N^6,N^6$-Tetramethylenadenosine 5.36 g of inosine was dissolved in 100 ml of hexamethyldisilazane and 0.5 ml of trimethylchlorosilane by heating the reaction mixture for 18 hours to 155°C. The reagents were distilled off, and the residue was agitated with 10 ml of pyrrolidine and 0.543 g. of mercury (II) chloride for 3 days at 120°C under a nitrogen atmosphere. After addition of further 0.543 g. of mercury (II) chloride the reaction mixture was agitated for 1 ½ days at 120°C. Then the reaction mixture was refluxed for 8 hours in 250 ml of methanol, decolorized with carbon and filtered hot. After concentration of the filtrate to 200 and 100 ml respectively, 3.56 g. (54% of therory) $N^6,N^6$-tetramethylenadenosine was obtained in 2 portions, m.p. 143°–144°C.

The preceding examples can be repeated wtih similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Process for the preparation of $N^6$-substituted adenosines of the general Formula I

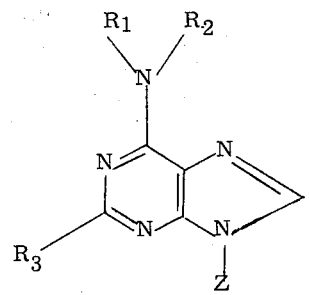

wherein $R_1$ and $R_2$ being the same or different represent hydrogen, alkyl of 1–6 carbon atoms, aralkyl of 7 to 10 carbon atoms unsubstituted or substituted with hydroxy or alkoxy with 1–4 carbon atoms, monocyclic carboxylic aryl unsubstituted or substituted with hydroxyl or a alkoxy with 1 to 4 carbon atoms, a heterocyclic ring of 4 to 7 ring members, containing a total of 1–3 nitrogen atoms, or an oxygen or sulfur atom; or when $R_1$ is hydrogen $R_2$ is hydroxyl, amino, alkyl or 1–4 carbon atoms substituted in the terminal position with a mono- or dialkylamino group, containing 1–4 carbon atoms in each alkyl group, or a mono- or bicyclic heterocyclic group of 5–10 members, containing a total of 1–3 hetero atoms, which can be nitrogen, oxygen and sulfur, or $R_1$ and $R_2$, together with the N-atom, collectively represent a heteromonocyclic ring of 4–7 members containing a total of 1–3 hetero atoms which, in addition to the nitrogen atom, can be nitrogen, oxygen or sulfur, unsubstituted or substituted by an alkyl group with 1–4 carbon atoms, $R_3$ represents hydrogen or amino, and Z represents a ribofuranosyl residue, said process comprising reacting a 6-trialkylsilyloxypurine derivate of the general Formula II

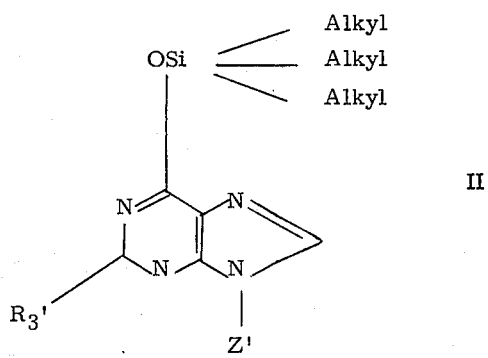

wherein the alkyl residues are the same and each alkyl is of 1 to 3 carbon atoms, $R_3'$ represents hydrogen or a trialkylsilylamino group wherein the alkyl is of 1 to 3 atoms, $Z'$ represents a silylated or carboxylic acid acylated sugar residue, or a sugar residue blocked by acetal formation, with a member selected from the group consisting of ammonia, an amine of the formula $HNR_1R_2$, wherein $R_1$ and $R_2$ have the above designations, and a salt of said amine, in the presence of a tertiary base.

2. The process of claim 1 wherein a Lewis acid is used as a catalyst.

3. The process of claim 1 wherein the reaction takes place in the presence of a tertiary amine.

4. The process of claim 1 wherein the reaction is conducted at a temperature of 0°–180°C.

5. The process of claim 1 wherein ammonia is a reactant and is conducted at a pressure of 20–50 atmospheres gauge.

6. A compound of the formula

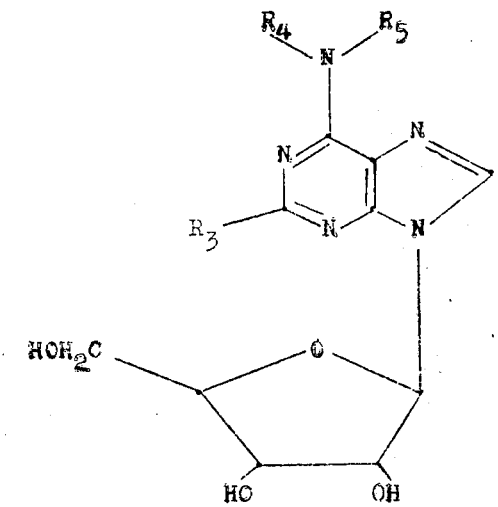

wherein
$R_3$ represents hydrogen or amino, and
$R_4$ and $R_5$, together with the N-atom, collectively represent a heteromonocyclic ring of 5–7 members containing a further oxygen- or nitrogen atom, the nitrogen atom being unsubstituted or substituted by a methyl group.

7. A compound of claim 6, 6-(4-N-methylpiperazino)-9-β-D-ribofuranosyl-purine.

8. A compound of claim 6, 6-(4-N-methylpiperazino)-2-amino-9-β-D-ribofuranosyl-purine.

9. A compound of claim 6, 6-morpholino-9-β-D-ribofuranosylpurine.

10. A compound of claim 6, 6-morpholino-2-amino-9-β-D-ribofuranosyl-purine.

* * * * *